United States Patent [19]

Uno et al.

[11] Patent Number: 4,530,930
[45] Date of Patent: Jul. 23, 1985

[54] ANTIMICROBIAL 1-ETHYL-6,8-DIFLUORO-1,4-DIHYDRO-7-(1-IMIDAZOLYL)-4-OXOQUINOLINE-3-CARBOXYLIC ACID DERIVATIVES

[75] Inventors: Toshio Uno, Daito; Masanori Takamatsu, Toyonaka; Koji Iuchi, Nara; Goro Tsukamoto, Toyonaka, all of Japan

[73] Assignee: Kanebo, Ltd., Tokyo, Japan

[21] Appl. No.: 562,735

[22] Filed: Dec. 19, 1983

[30] Foreign Application Priority Data

Dec. 29, 1982 [JP] Japan .................. 57-234595

[51] Int. Cl.³ ............... C07D 401/04; A61K 31/415; A61K 31/47
[52] U.S. Cl. ..................... 514/312; 546/156
[58] Field of Search .................. 546/156; 424/258

[56] References Cited

U.S. PATENT DOCUMENTS 3,673,193  6/1972  Lesher ................ 260/295.5 B
3,907,808  9/1975  Lesher ................ 260/287
4,398,029  8/1983  Irikura ................ 544/363

FOREIGN PATENT DOCUMENTS 2656574  6/1978  Fed. Rep. of Germany .
88182  6/1982  Japan .

Primary Examiner—Donald G. Daus
Assistant Examiner—Robert Benson
Attorney, Agent, or Firm—Wegner & Bretschneider

[57] ABSTRACT

1-Ethyl-6,8-difluoro-1,4-dihydro-7-(1-imidazolyl)-4-oxoquinoline-3-carboxylic acid derivative of the formula:

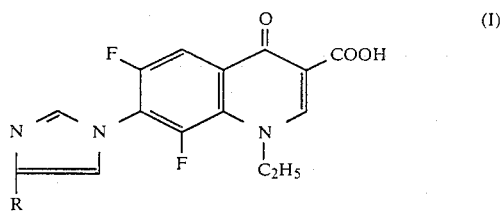

wherein R is hydrogen atom or an alkyl group having 1 to 3 carbon atoms, which have excellent anti-microbial activities and are useful as an anti-microbial agent for the treatment of infectious diseases in warm-blooded animals including human beings, and an anti-microbial composition containing said compound as an active ingredient.

6 Claims, No Drawings

ANTIMICROBIAL 1-ETHYL-6,8-DIFLUORO-1,4-DIHYDRO-7-(1-IMIDAZOLYL)-4-OXOQUINOLINE-3-CARBOXYLIC ACID DERIVATIVES

The present invention relates to novel 1-ethyl-6,8-difluoro-1,4-dihydro-7-(1-imidazolyl)-4-oxoquinoline-3-carboxylic acid derivatives of the formula:

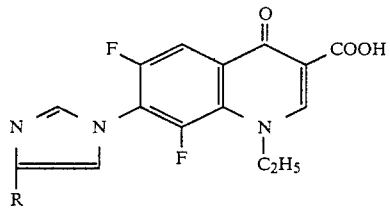

wherein R is hydrogen atom or an alkyl group having 1 to 3 carbon atoms, and an anti-microbial composition comprising as an active ingredient the above compound (I).

The compounds (I) of the present invention have excellent anti-microbial activities and are useful for protecting warm-blooded animals including human beings from microbial infections.

Since it has been found that nalidixic acid is useful as an anti-microbial agent, pyridonecarboxylic acid anti-microbial agents have mainly been used as a synthetic anti-microbial agent instead of sulfonamide preparations. As such an agent, there have widely been used piromidic acid, pipemidic acid as well as nalidixic acid. These anti-microbial agents have excellent anti-microbial activities against gram negative bacteria and hence are usually used as an agent for treating urinary infections, but are not sufficiently effective against gram positive bacteria. In order to find an anti-microbial agent effective for a wide range of microorganisms, various pyridonecarboxylic acid compounds have been synthesized and studied for their anti-microbial activities, among which 1-ethyl-1,4-dihydro-6-fluoro-4-oxo-7-(1-piperazinyl)quinoline-3-carboxylic acid (compound A) and 1-ethyl-1,4-dihydro-6-fluoro-7-[1-(4-methylpiperazinyl)]-4-oxoquinoline-3carboxylic acid (compound B) of the following formulae have been attracted by persons in this field because of their wide range of anti-microbial spectrum (cf. U.S. Pat. No. 4,146,719, and U.S. Pat. No. 4,292,317).

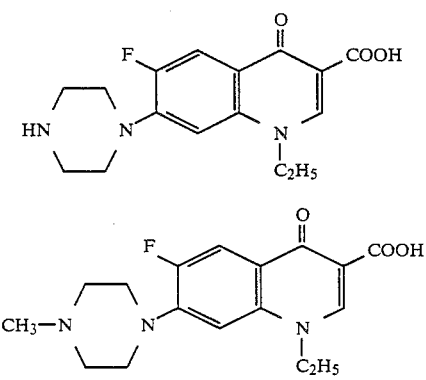

Moreover, there have recently been reported 1-ethyl-6,8-difluoro-1,4-dihydro-4-oxo-7-(1-piperazinyl)quinoline-3-carboxylic acid (compound C) and 1-ethyl-6,8-difluoro-1,4-dihydro-7-[1-(4-methylpiperazinyl)]-4-oxoquinoline-3-carboxylic acid (compound D) of the following formulae (cf. U.K. patent application No. 2,057,440):

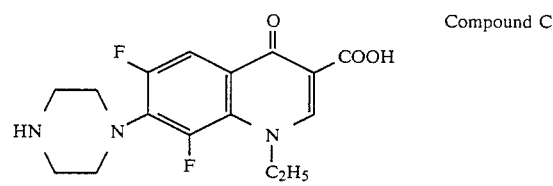

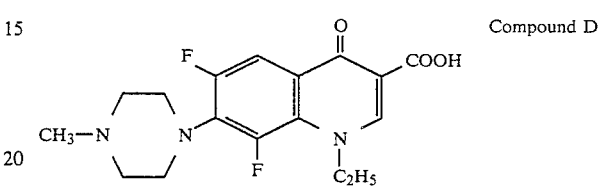

These 6-fluoro compounds and 6,8-difluoro compounds are effective against both gram negative and gram positive bacteria and show more potent anti-microbial activities and wider anti-microbial spectrum in comparison with nalidixic acid, piromidic acid and pipemidic acid. However, these compounds show insufficient bioavailability when administered orally as is clear from Experiments 2 and 3 as disclosed hereinafter.

An object of the present invention is to provide novel compounds useful as an anti-microbial agent. Another object of the invention is to provide novel fluorine-containing quinolinecarboxylic acid derivatives having excellent anti-microbial activity in vitro and high absorbability by oral administration with less toxicity. A further object of the invention is to provide an anti-microbial agent containing as an active ingredient the above novel compounds, which are useful for the treatment of various infections.

The fluorine-containing quinolinecarboxylic acid derivatives of the present invention include the compounds of the formula (I) and a pharmaceutically acceptable salt thereof.

The pharmaceutically acceptable salt includes a salt at the carboxyl group of the compounds (I) and also an acid addition salt at the imidazolyl group of the compounds (I). The former salt includes, for example, metal salts such as sodium salt, potassium salt, and calcium salt, and the latter salt includes, for example, inorganic salts such as hydrochloride and sulfate.

The compounds of the present invention show excellent anti-microbial activities, i.e. similar minimal inhibitory concentration (MIC) to that of the known compounds A to D in vitro test and show far greater bioavailability than that of the known compounds A to D when administered orally, as is clear from Experiments 1 to 3 as disclosed hereinafter. Moreover, the compounds of the present invention show less toxicity (cf. Experiment 4 as disclosed hereinafter). Accordingly, the compounds of the present invention are useful as an anti-microbial agent against various infections.

The compounds of the present invention are characteristic in the chemical structure that they have an imidazolyl substituent at the 7-position thereof. As a pyridonecarboxylic acid compound having an imidazolyl substituent at 7-position, there are known 1-ethyl-1,4-dihydro-7-(1-imidazolyl)-4-oxo-1,6-naphthylidine-3- carboxylic acid (compound E) and 2,3-dihydro-9-fluoro-10-(1-imidazolyl)-3-methyl-7-oxo-7H-pyrido[1,2,3-de][1,4]benzoxazine-6-carboxylic acid (compound F) of the following formulae (cf. German Patent Offenlegungsschrift No. 26 56 574, and Japanese Laid Open Patent Application No. 88182/1982):

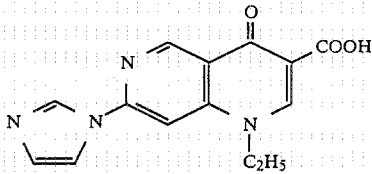

Compound E

I-a: 1-Ethyl-6,8-difluoro-1,4-dihydro-7-(1-imidazolyl)-4-oxoquinoline-3-carboxylic acid (in the formula (I), R=H; the compound of Example 1)

I-b: 1-Ethyl-6,8-difluoro-1,4-dihydro-7-[1-(4-methylimidazolyl)]-4-oxoquinoline-3-carboxylic acid (in the formula (I), R=CH$_3$, the compound of Example 2)

(Reference compounds)

Compound A, compound B, compound C, compound D, compound E and compound F as mentioned hereinbefore.

(2) Test method:

In accordance with the method as disclosed in Chemotherapy, Vol. 29, pages 76–79 (1981), MIC (μg/ml) of each test compound was measured.

(3) Results:

The test results are shown in Table 1.

TABLE 1

| Microorganisms | Gram positive or negative | MIC (μg/ml) | | | | | | | |
| --- | --- | --- | --- | --- | --- | --- | --- | --- | --- |
| | | Compounds of this invention | | Reference compounds | | | | | |
| | | I-a | I-b | A | B | C | D | E | F |
| Staphylococcus aureus FDA 209P JC-1 | + | 0.39 | 0.78 | 0.39 | 0.39 | 0.39 | 0.78 | >100 | 0.19 |
| Staphylococcus epidermidis | + | 3.13 | 3.13 | 3.13 | 0.78 | 3.13 | 1.56 | >100 | 1.56 |
| Bacillus subtilis ATCC 6633 | + | 0.10 | 0.05 | 0.39 | 0.20 | 0.39 | 0.20 | 100 | 0.10 |
| Escherichia coli NIHJ JC-2 | − | 0.20 | 0.39 | 0.39 | 0.39 | 0.20 | 0.20 | >100 | 0.39 |
| Klebsiella pneumoniae PCI-602 | − | 0.05 | 0.10 | 0.10 | 0.10 | 0.10 | 0.10 | 25 | 0.05 |
| Serratia marcescens IAM 1184 | − | 1.56 | 3.13 | 0.39 | 0.39 | 0.78 | 0.78 | 100 | 3.12 |
| Proteus Vulgaris HX-19 | − | 0.025 | 0.025 | 0.10 | 0.10 | 0.10 | 0.05 | 3.12 | 0.025 |
| Pseudomonas aeruginosa IFO 3445 | − | 6.25 | 6.25 | 1.56 | 1.56 | 0.78 | 1.56 | >100 | 3.12 |
| Salmonella paratyphi 1015 | − | 0.05 | 0.10 | 0.10 | 0.10 | 0.10 | 0.10 | 12.5 | 0.05 |

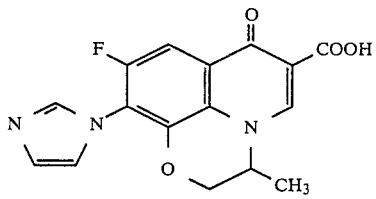

Compound F

However, these compounds are clearly distinguished from the compounds of the present invention in that the nucleous structure is 1,6-naphthylidine ring (in compound E) and a tricyclic structure (in compound F). Moreover, compound E shows less antimicrobial activities in vitro test (cf. Experiment 1 as disclosed hereinafter), and compound F is inferior to the compounds of the present invention in the bioavailability when administered orally. (cf. Experiment 2 as disclosed hereinafter).

In order to show the excellent effects of the compounds of the present invention, the following experiments have been done.

Experiment 1

(1) Test compounds:

(Compounds of the present invention)

Experiment 2

(Bioavailability in oral administration in mice)

(1) Test compounds:

The same compounds as used in Experiment 1 except compound E were used (compound E was omitted from this experiment because it showed far less activities).

(2) Test method:

Each of the test compounds was suspended in a 0.5% sodium carboxymethylcellulose to prepare a suspension having a concentration of 5 mg/ml of the compound.

ddY-strain male mice (5 week old, weighing 22 to 25 g, three per group) were used. The suspension was orally administered to mice fasted for 16 hours. The dose of the test compound was adjusted to 50 mg/kg of body weight of animal. 30, 60, 120, and 240 minutes after the administration of the test compound, blood was taken out from each mouse, and the blood sample thus obtained was centrifuged at 3,000 rpm for 20 minutes to obtain a serum sample. Concentration (μg/ml) of test compound in the serum sample was measured by a bioassay method on Klebsiella pneumoniae IFO 3512, and also the areas under the curve (AUC, μg.hour/ml) was calculated from the figure of the concentration in serum.

(3) Results:

The concentration in serum and AUC of the test compound are shown in Table 2.

TABLE 2

| Compound | Concentration in serum (μg/ml) | | | | AUC (μg · hr/ml) 1–4 hrs. |
|---|---|---|---|---|---|
| | After 30 min. | 60 min. | 120 min. | 240 min. | |
| I-a | 44.8 ± 8.9 | 39.3 ± 5.2 | 7.6 ± 1.7 | 1.7 ± 0.5 | 64.9 |
| I-b | 49.2 ± 2.5 | 29.4 ± 2.5 | 10.0 ± 0.8 | 6.3 ± 1.1 | 67.9 |
| A | 1.05 ± 0.24 | 0.69 ± 0.07 | 0.40 ± 0.05 | 0.36 ± 0.03 | 2.0 |
| B | 12.2 ± 2.5 | 5.4 ± 0.6 | 3.5 ± 0.6 | 2.3 ± 0.2 | 17.8 |
| C | 6.26 ± 1.57 | 3.51 ± 1.29 | 3.41 ± 0.67 | 1.53 ± 0.27 | 12.4 |
| D | 14.4 ± 0.8 | 11.5 ± 0.9 | 6.7 ± 0.6 | 3.4 ± 0.4 | 29.3 |
| F | 6.4 ± 1.8 | 2.6 ± 1.0 | 1.2 ± 0.3 | 0.6 ± 0.2 | 7.5 |

Experiment 3

(Bioavailability in oral administration in rats)

(1) Test compounds:

The compound I-a, compound I-b, compound A, compound B, compound C and compound D were used.

(B 2) Test method:

Each of the test compounds was suspended in a 0.5% sodium carboxymethylcellulose to prepare a suspension having a concentration of 5 mg/ml of the test compound.

Wistar-strain male rats (weighing 160 g ±20 g, three per group) were used. The suspension was orally administered to rats fasted 16 hours. 30, 60, 120, and 240 minutes after the administration of the test compound, blood was taken out from the rats. The blood was centrifuged at 3,000 rpm for 20 minutes to obtain a plasma sample. In the same manner as described in Experiment 2, the concentration (μg/ml) of test compound in plasma and also AUC (μg.hr/ml) were measured.

(3) Results:

The results are shown in Table 3.

TABLE 3

| Compound | Concentration in plasma (μg/ml) | | | | AUC (μg · hr/ml) 1–4 hrs. |
|---|---|---|---|---|---|
| | After 30 min. | 60 min. | 120 min. | 240 min. | |
| I-a | 54.9 ± 3.9 | 70.8 ± 3.1 | 48.0 ± 4.3 | 31.3 ± 3.6 | 183.9 |
| I-b | 58.7 ± 5.3 | 62.9 ± 6.0 | 52.0 ± 4.0 | 33.5 ± 4.9 | 188.0 |
| A | 1.81 ± 0.14 | 1.19 ± 0.02 | 0.63 ± 0.11 | 0.25 ± 0.01 | 2.99 |
| B | 11.8 ± 1.1 | 14.2 ± 0.8 | 7.8 ± 0.3 | 5.0 ± 0.3 | 33.2 |
| C | 11.7 ± 1.1 | 12.3 ± 0.8 | 6.4 ± 0.3 | 2.0 ± 1.8 | 26.0 |
| D | 22.6 ± 4.5 | 24.0 ± 2.3 | 14.6 ± 1.1 | 9.3 ± 0.1 | 60.45 |

Experiment 4

(Acute toxicity: $LD_{50}$)

(1) Test compounds:

The compound I-a, compound I-b, compound B, compound C and compound D were used.

(2) Test method:

The acute toxicities in oral administration and intravenous injection of the test compounds were tested as follows:

In oral administration: To ddY-strain male mice (weighing 20-25 g, five per group) was administered orally a suspension of each test compound in a 0.5% sodium carboxymethylcellulose. One week after the administration of the test compound, the 50% lethal dose ($LD_{50}$) was determined in accordance with the Weil method [cf. J. Biometric Soc., 8, 249 (1959)].

In intravenous administration: Each of the test compounds was dissolved in 1N aqueous sodium hydroxide solution and thereto was added a phosphoric acid-saline buffer (pH 7.2) to prepare a test solution. The test solution was intravenously injected to ddy-strain male mice (weighing 20-25 g, five per group). One week after the administration of the test solution, the $LD_{50}$ was determined in accordance with Weil method.

(3) Results:

The results are shown in Table 4.

TABLE 4

| Compound | $LD_{50}$ (mg/kg) | |
|---|---|---|
| | p.o. | i.v. |
| I-a | >4,000 | 773 |
| I-b | >4,000 | 593 |
| A | (>4,000)* | (220)* |
| B | >4,000 | 555 |
| C | 1,072 | 193 |
| D | 536 | 196 |

*The data were reported at Nippon Kagakuryoho-gakkai 28th Meeting (1980, Tokyo)

From the above experimental results, it is clear that the compounds of the present invention have excellent anti-microbial activities and also high bioavailability with less toxicity and hence are useful as an antimicrobial agent with high safety.

The compounds (I) of the present invention can be prepared by reacting 1-ethyl-1,4-dihydro-4-oxo-6,7,8-trifluoroquinoline-3-carboxylic acid of the formula (II) and an imidazole compound of the formula (III) as shown in the following reaction scheme:

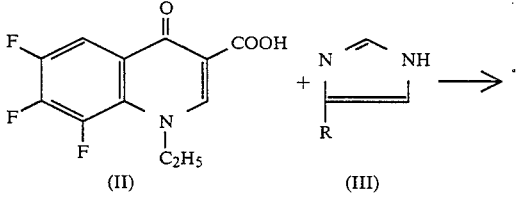

-continued

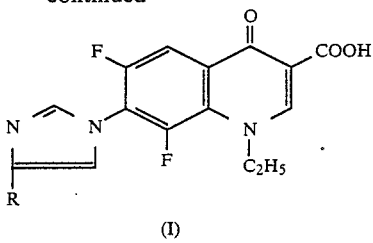

wherein R is as defined above.

The starting compound (II) is known and is disclosed in U.K. patent application No. 2,057,440, and the other starting compound (III) is also known and is disclosed in J. Indian Chem. Soc., 38, 853 (1961) and Ber., 15, 1493 (1882).

The reaction of the compound (II) and the compound (III) is preferably carried out in a polar solvent, such as methanol, ethanol, pyridine, dimethylformamide, or dimethylsulfoxide. The compound (III) is used in an amount of 1 to 5 moles, preferably 1.5 to 3 moles, per 1 mole of the compound (II). The reaction temperature is usually in the range of 40° to 200° C., preferably 50° to 150° C. Too high reaction temperature is not suitable because of tendency of producing by-products. The reaction is usually completed in 1 to 10 hours under the above reaction conditions.

The compounds (I) obtained by the above reaction can be isolated from the reaction mixture and purified by conventional purification methods, such as a recrystallization method. When required, the compounds (I) may be converted into a pharmaceutically acceptable salt thereof by treating them with a corresponding base or acid in a usual manner.

The compounds (I) or their pharmaceutically acceptable salts of the present invention are preferably administered orally to patients as an anti-microbial agent. For oral administration, they are prepared in the form of conventional preparations such as tablets, granules, fine granules, powders or syrups, in admixture with conventional non-toxic, pharmaceutically acceptable carriers such as corn starch, lactose, magnesium stearate, microcrystalline cellulose, kaoline, calcium carbonate, talc, or the like, and further in the form of a capsule which is prepared by packing the above fine granules or powders into a capsule.

The dosage of the compounds of the present invention may vary according to age and weight of the patients and severity of disease, but is usually in the range of 1 to 50 mg/kg/day, which is preferably administered by dividing two to four times per day.

The present invention is illustrated by the following Examples but should not be construed to be limited thereto.

EXAMPLE 1

Preparation of 1-ethyl-6,8-difluoro-1,4-dihydro-7-(1-imidazolyl)-4-oxoquinoline-3-carboxylic acid [I-a]:

To 1-ethyl-6,7,8-trifluoro-1,4-dihydro-4-oxoquinoline-3-carboxylic acid (13.6 g) and imidazole (10.2 g) is added dimethylformamide (80 ml), and the mixture is stirred at 100° C. for 1.25 hour. The reaction mixture is cooled to room temperature, and the precipitated crystals are separated by filtration and washed with ethanol. The crude crystals thus obtained are recrystallized from dimethylformaide to give the title compound (7.7 g) as colorless needles. Melting point: 283°–288° C. (decomp. with foam), being gradually colored from about 245° C. IR (KBr, $\nu_{C=O}$): near 1720 cm$^{-1}$.

Elementally analysis for $C_{15}H_{11}F_2N_3O_3$:

Calcd (%): C,56.43; H,3.47; N,13.16; Found (%): C,56.54; H,3.49; N,13.03.

EXAMPLE 2

Preparation of 1-ethyl-6,8-difluoro-1,4-dihydro-7-[1-(4-methylimidazolyl)]-4-oxoquinoline-3-carboxylic acid [I-b]:

To 1-ethyl-6,7,8-trifluoro-1,4-dihydro-4-oxoquinoline-3-carboxylic acid (20 g) and 4-methylimidazole (12.5 g) is added dimethylsulfoxide (300 ml), and the mixture is stirred at 110°–115° C. for 1 hour. To the reaction mixture is added water (1 liter), and the precipitated crystals are separated by filtration and recrystallized form ethanol to give the title compound (12.8 g) as colorless needles. Melting point: 247°–253° C., IR (KBr, $\nu_{C=O}$): near 1722 cm$^{-1}$.

Elementary analysis for $C_{16}H_{13}F_2N_3O_3 \cdot \frac{1}{2}H_2O$:

Calcd (%): C,56.14; H,4.12; N,12.28; Found (%): C,55.94; H,4.09; N,12.27.

EXAMPLE 3

Preparation of tablets:

| Components | |
|---|---|
| Active ingredient (Compound I-a) | 250 g |
| Cornstarch | 46 g |
| Microcrystalline cellulose | 100 g |
| Magnesium stearate | 4 g |
| | 400 g |

Procedure

The active ingredient, cornstarch and microcrystalline cellulose are mixed with water and the mixture is kneaded. The kneaded mixture is passed through a net to prepare granules, followed by drying. The granules thus prepared are mixed with magnesium stearate and then tableted to give tablets (weight of one tablet: 400 mg) which contain 250 mg of the active ingredient per one tablet.

EXAMPLE 4

Preparation of granules:

| Components | |
|---|---|
| Active ingredient (Compound I-b) | 250 g |
| Lactose | 235 g |
| Cornstarch | 109 g |
| Hydroxypropyl cellulose | 6 g |
| | 600 g |

Procedure

The active ingredient and cornstarch are mixed well and thereto is added a solution of hydroxypropyl cellulose in water (120 ml), and the mixture is sufficiently kneaded. The kneaded product thus obtained is passed through a net (20 mesh) to granulate, and the granules are dried and regulated their particle size to give the desired granules.

EXAMPLE 5

Preparation of capsules:

| Components | |
|---|---|
| Active ingredient (Compound I-a) | 250 g |
| Cornstarch | 60 g |
| Lactose | 35 g |
| Magnesium stearate | 5 g |
| | 350 g |

Procedure

The above components are well mixed, and the mixture (each 350 mg) is packed in a capsule to give the desired capsules which contain the active ingredient of 250 mg per one capsule.

What is claimed is:

1. A 1-ethyl-6,8-difluoro-1,4-dihydro-7-(1-imidazolyl)-4-oxoquinoline-3-carboxylic acid compound of the formula:

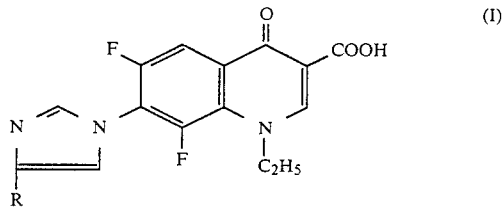

wherein R is hydrogen atom or an alkyl group having 1 to 3 carbon atoms.

2. The compound according to claim 1, wherein R is hydrogen atom.

3. The compound according to claim 1, wherein R is methyl group.

4. An anti-microbial composition, which comprises as an active ingredient a 1-ethyl-6,8-difluoro-1,4-dihydro-7-(1-imidazolyl)-4-oxoquinoline-3-carboxylic acid compound of the formula:

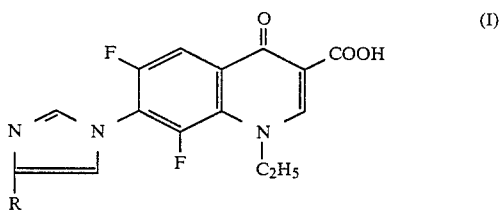

wherein R is hydrogen atom or an alkyl group having 1 to 3 carbon atoms, in admixture with a pharmaceutically acceptable carrier or diluent.

5. The composition according to claim 4, wherein R is hydrogen atom.

6. The composition according to claim 4, wherein R is methyl group.

* * * * *